(12) United States Patent
Sueda et al.

(10) Patent No.: US 10,828,144 B2
(45) Date of Patent: Nov. 10, 2020

(54) STENT GRAFT

(71) Applicants: Hiroshima University, Hiroshima (JP); Goodman Co., Ltd., Aichi (JP)

(72) Inventors: Taijiro Sueda, Hiroshima (JP); Shinya Takahashi, Hiroshima (JP)

(73) Assignees: Hiroshima University, Hiroshima (JP); Goodman Co., Ltd., Aichi (JP)

( * ) Notice: Subject to any disclaimer, the term of this patent is extended or adjusted under 35 U.S.C. 154(b) by 767 days.

(21) Appl. No.: 14/381,392

(22) PCT Filed: Feb. 27, 2013

(86) PCT No.: PCT/JP2013/055066
§ 371 (c)(1),
(2) Date: Aug. 27, 2014

(87) PCT Pub. No.: WO2013/129445
PCT Pub. Date: Sep. 6, 2013

(65) Prior Publication Data
US 2015/0127086 A1    May 7, 2015

(30) Foreign Application Priority Data
Feb. 27, 2012 (JP) ................... 2012-040771

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2230/0008* (2013.01);
(Continued)

(58) Field of Classification Search
CPC ........................................................ A61F 2/07
See application file for complete search history.

(56) References Cited

U.S. PATENT DOCUMENTS

| | | |
|---|---|---|
| 2001/0049553 A1 | 12/2001 | De Paulis |
| 2003/0139805 A1 | 7/2003 | Holmberg et al. |

(Continued)

FOREIGN PATENT DOCUMENTS

| | | |
|---|---|---|
| CN | 2726558 Y | 5/2005 |
| CN | 200970283 Y | 11/2007 |

(Continued)

OTHER PUBLICATIONS

Chinese Office Action for Application No. 201380011126.2 dated Jun. 24, 2015.

(Continued)

*Primary Examiner* — Matthew W Schall
(74) *Attorney, Agent, or Firm* — K&L Gates LLP; Louis C. Cullman; Georgia N. Kefallinos (57) ABSTRACT

The stent graft (10) comprises a cylinder comprising a graft material in the form of a film and a stent that supports the cylinder. Further, the stent graft (10) is inserted within a region from the ascending aorta to the sinus of valsalva, and the stent graft comprises cylindrical body section (11) arranged in the ascending aorta and the sinus of valsalva section (12) arranged in the sinus of valsalva and having an inner diameter larger than that of the body section (11).

6 Claims, 12 Drawing Sheets

(52) U.S. Cl.
CPC ........... *A61F 2230/0013* (2013.01); *A61F 2250/0039* (2013.01); *A61F 2250/0098* (2013.01)

(56) References Cited

U.S. PATENT DOCUMENTS

| | | | |
|---|---|---|---|
| 2004/0260389 A1* | 12/2004 | Case | A61F 2/2418 623/1.24 |
| 2008/0132993 A1* | 6/2008 | Rasmussen | A61F 2/06 623/1.13 |
| 2008/0140110 A1* | 6/2008 | Spence | A61F 2/06 606/200 |
| 2011/0087318 A1 | 4/2011 | Daugherty et al. | |
| 2012/0035714 A1 | 2/2012 | Ducke et al. | |

FOREIGN PATENT DOCUMENTS

| | | |
|---|---|---|
| CN | 201042472 | 4/2008 |
| CN | 102125475 A | 7/2011 |
| JP | 2005-521471 A | 7/2005 |
| JP | 2007-181701 | 7/2007 |
| JP | 2007-185506 | 7/2007 |
| JP | 2009-506842 A | 2/2009 |
| JP | 2009-539477 | 11/2009 |
| JP | 2010-512231 | 4/2010 |
| WO | 1999/039663 A1 | 8/1999 |
| WO | 2009082654 | 7/2009 |
| WO | 2011/056797 A1 | 5/2011 |
| WO | 2012067821 | 11/2012 |

OTHER PUBLICATIONS

Supplemental European Search Report for Application No. 13754454.0 dated Jul. 23, 2015.
Office Action dated Mar. 14, 2016 for Chinese Patent Application 201380011126.2.
Office Action dated Sep. 6, 2016 for Japanese Patent Application 2014-502277.
Japanese Office Action drafted on Feb. 1, 2018 for Japanese Patent Application No. 2017-062046.
Extended European Search Report dated Jan. 5, 2018 for European Patent Application No. 17193204.9.

* cited by examiner

STENT GRAFT

TECHNICAL FIELD

The present disclosure relates to stent grafts.

BACKGROUND ART

Aortic diseases include cases of aortic aneurysms and aortic dissections. The aortic aneurysm refers to generation of aneurysm which bulges out like a lump in a part of the aorta; and arteriosclerosis is thought to be the main cause of the onset of the aortic aneurysm. The aortic aneurysm is a dangerous disease that exhibits no noticeable subjective symptoms such as pain even when the enlargement of the aortic aneurysm advanced and causes the rupture of the aorta in the course of time due to failure to withstand blood pressure, resulting in massive bleeding. Further, the aortic dissection is a disease in which some unknown trigger causes blood to flow into the membrane of the middle layer (tunica media) of three layers structuring the aorta, forcing the layer structures apart.

In the treatment of abdominal aortic aneurysm or the like, endovascular aortic repair has been recently carrying out (for example, Patent Literatures 1 and 2). A stent graft is composed of a cylinder made of a biocompatible graft material and a stent that supports the cylinder and function as a synthetic blood vessel. In the endovascular aortic repair, the stent graft is contracted and housed within a catheter, which is inserted in the aorta and moved to an affected area, followed by removal of the stent graft out of the catheter. The stent graft is extended via the force of stent's metal spring and patient's own blood pressure and becomes stick to the inner wall of blood vessels. The endovascular aortic repair is superior also in terms of invasiveness because there is no requirement for wide incision of the chest or abdominal cavity, which incision is required in surgical operations.

There is acute type A aortic dissection as a fatal disease among diseases occurring in the ascending aorta. Blood flows between the tunica adventitia and tunica media of the aorta and thereby the circulation of blood deteriorates. In addition, fatal cases where the ascending aorta raptures within 48 hours of the onset account for about 50% and it is thus the most severe disease among the aortic diseases. Because of this, once diagnosed with acute type A dissociation, a patient is taken to an operation room as soon as possible regardless of day and night and undergoes surgery that involves connection of extracorporeal circulation to stop the heart, incision of the ascending aorta, closure of the dissection cavity, and replacement with a synthetic blood vessel. But, the operative mortality rate is still as high as about 10%.

Further, among thoracic aortic aneurysms, there is, as the most common disease, aortic arch aneurysm in which a sac-like aneurysm is formed in the aortic arch. The aortic arch aneurysm is an aortic aneurysm of a region where blood vessels sending blood to the brain are branched (the brachiocephalic artery, left common carotid artery, and left subclavian artery).

CITATION LIST

Patent Literature

Patent Literature 1: Unexamined Japanese Patent Application Kokai Publication No. 2007-181701

Patent Literature 2: Unexamined Japanese Patent Application Kokai Publication No. 2007-185506

SUMMARY OF INVENTION

Technical Problem

For the treatment of the ascending aorta such as the treatment of acute type A aortic dissection, endovascular aortic repair has not been attempted thus far. The reasons for that include the following. The stent graft is usually used in the treatment of aortic aneurysm by inserting a guide wire and a sheath catheter that encloses the stent graft from the aorta of the lower limb. But, in acute type A aortic dissection, dissection cavity intricately runs in a region from the descending aorta to the iliac aorta. Because of this, it is difficult to insert the guide wire and stent graft from the aorta of the lower limb to the true lumen of the aorta; and a forced attempt of insertion may falsely leads the stent graft to enter into the dissection cavity, resulting in a high risk of aortic rupture.

In addition, with regard to the treatment of aortic arch aneurysm, endovascular aortic repair has not been attempted thus far either. The reasons for that include the following. The aortic arch aneurysm occurs in the lesser curvature side of the arch and there are, in the greater curvature thereof, openings branching toward brachiocephalic artery, left common carotid artery, and left subclavian artery. Use of usual stent grafts ends up occluding these openings and disabling blood to circulate to the brain.

The present disclosure was made in the light of the above matters; and an object thereof is to provide stent grafts that can be used in the treatment of ascending aorta. Further, another object is to provide stent grafts that do not close the openings of arteries branching from the periphery of aneurysm in aortic arch aneurysm or the like.

Solution to Problem

The stent graft according to the first aspect of the present invention comprises a cylinder comprising a graft material in the form of a film, and a stent which supports the cylinder, characterized in that:

the stent graft is inserted within a region from ascending aorta to sinus of valsalva; and the stent graft comprises a cylindrical body section arranged in the ascending aorta, and a sinus of valsalva section arranged in the sinus of valsalva and having an inner diameter larger than that of the body section.

The sinus of valsalva section preferably has a length shorter than the length from the boundary between the sinus of valsalva and the ascending aorta to the opening of coronary artery.

The body section preferably has a length shorter than the length from the boundary between the sinus of valsalva and the ascending aorta to the opening of brachiocephalic artery.

Roentgen markers may be arranged at the boundary between the body section and the sinus of valsalva section.

The stent graft according to the second aspect of the present invention comprises a cylinder comprising a graft material in the form of a film, and a stent which supports the cylinder, characterized in that:

an open window is formed in the cylinder; and roentgen markers are arranged around the periphery of the open window.

The roentgen markers are preferably arranged at the inside of the open window.

The open window is preferably circular when the stent graft is extended, and the roentgen markers are preferably arranged in four directions of the open window.

The roentgen markers may be soldered to the stent.

The stent graft is inserted in aortic arch; and the open window is preferably formed so as to enclose the openings of left subclavian artery, left common carotid artery, and brachiocephalic artery branching from the aortic arch.

Advantageous Effects of Invention

The stent graft according to the first aspect of the present disclosure has a sinus of valsalva section and body section, and the body section occludes a tear generated in the aorta and the sinus of valsalva section concurrently functions as a stopper; and thus can be used in the treatment of aortic dissection that occurs in the ascending aorta.

The stent graft according to the second aspect of the present disclosure has an open window and roentgen markers around the periphery of stent graft's open window; and the position of open window can be readily recognized even in a state where the stent graft is contracted and housed within a sheath catheter. Thereby, even when the stent graft is used in a region where the openings of arteries branching from the periphery of the aneurysm such as aortic arch aneurysm are present, the stent graft can be readily placed in an appropriate position and is at low risk of occluding the openings of the branching arteries, which is advantageous.

BRIEF DESCRIPTION OF DRAWINGS

FIG. 2 is a cross sectional view taken along line A-A' of FIG. 1.

DESCRIPTION OF EMBODIMENTS

Embodiment 1

While referring to the figures, the stent graft according to Embodiment 1 will be described. The stent graft 10 according to the present embodiment is inserted within a region from the sinus of valsalva of the ascending aorta to the brachiocephalic aorta and used mainly in the treatment of aortic dissection of the ascending aorta.

Figure 1:
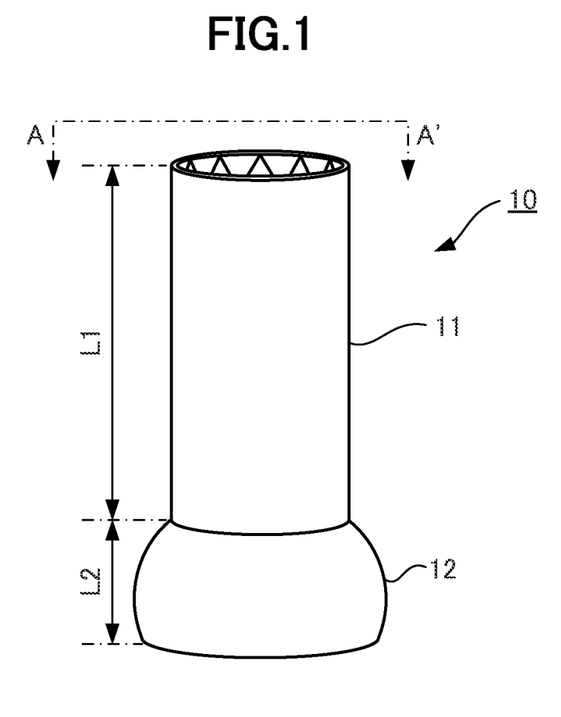
FIG. 1 is a perspective view of the stent graft according to Embodiment 1.
Figure 2A:
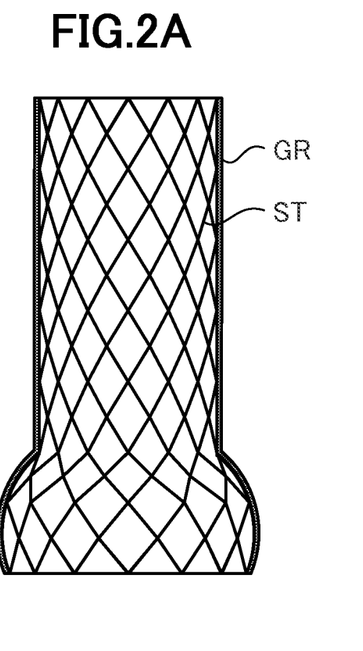
FIG. 2A is a figure showing a state where the stent graft is extended and FIG. 2B is a figure showing a state where the stent graft is contracted.

As shown in FIG. 1 and FIG. 2A, the stent graft 10 comprises the body section 11 and the sinus of valsalva section 12. The body section 11 and the sinus of valsalva section 12 are integrally formed, which is a hollow interior cylinder with the opening in the body section 11 side communicating into the opening in the sinus of valsalva section 12 side. The stent graft 10 functions as a synthetic blood vessel; and blood flows in the sinus of valsalva section 12 and body section 11 in the order mentioned.

The body section 11 is arranged in the ascending aorta and is a section that functions to occlude a tear (entry) generated in the ascending aorta. The body section 11 is in the form of circular cylinder and is formed so as to have an inner diameter that is almost the same as or slightly larger than the inner diameter of the ascending aorta. In addition, the length of the body section 11, L1, is formed to be shorter than the length from the sinus of valsalva to the brachiocephalic artery (the length shown in FIG. 3, La) so as not to occlude the opening of the brachiocephalic artery.

The sinus of valsalva section 12 is arranged in the sinus of valsalva and is a section that functions as a stopper such that the stent graft 10 placed in the ascending aorta does not slip out of position in the ascending aorta. The sinus of valsalva section 12 is formed so as to have an inner diameter larger than that of the body section 11. And, the shape of the sinus of valsalva section 12 is a shape corresponding to that of the sinus of valsalva; and the cross sectional shape thereof is substantially the form of bowl.

As for the sinus of valsalva section 12, it is required that the tip of the sinus of valsalva section 12 does not interfere with opening and closing of the aortic valve when the stent graft 10 is placed and further that it does not close the opening region of the right and left coronary arteries branching from the sinus of valsalva. Therefore, the length of the sinus of valsalva section 12, L2, is formed so as to be shorter than the length from the boundary between the sinus of valsalva and the ascending aorta to the openings of the right and left coronary arteries (the length of shown in FIG. 3, Lb). Further, combination of the stent graft 10 with a transcatheter aortic valve enables the aortic valve and ascending aorta to be simultaneously replaced.

And, the stent graft 10 comprises the graft material GR which is in the form of a cylinder and the stent ST that supports the graft material GR from the inside.

The stent ST is formed in the form of a cylinder having a spring property. The stent ST is formed so as to be able to be contracted and extended in a radial direction with the axis of the form of the cylinder as a center. The stent ST may be formed by any style as long as it can be contracted and extended in a radial direction; and examples thereof include one formed by placing several cells apart in a direction of the axis of a cylinder, the cell being folded in a zig-zag manner to form a circular shape, one formed by linking plural cells by soldering, and one formed by cutting a metal cylinder using a laser.

Examples of materials of the stent ST include 316L stainless steel which is stainless steel for medical applications, tantalum, cobalt alloy, and nickel titanium alloy.

Further, the stent ST is connected by a known technique including suture by cyclic yarns or the like so as not to fall off from the graft material GR.

The graft material GR comprises a biocompatible material in the form of a film such as PTFE (Poly Tetra Fluoro Ethylene) film, silicon film, polyurethane film, or polyester film The graft material GR is collapsible following stent ST's contraction and extension in a radial direction.

Figure 2B:
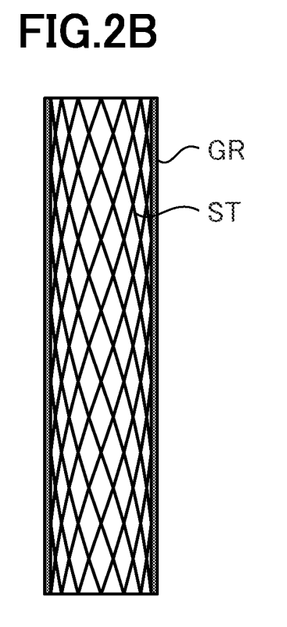

By the above composition, as shown in FIG. 2B, the stent graft 10 is altogether contracted when compressed in a radial direction with the axis of the cylinder as a center. Thereby, the stent graft 10 can be housed within a sheath catheter and, at the same time, can become stick to the inner wall of the ascending aorta when extended.

Subsequently, endovascular aortic repair using the stent graft 10 in the treatment of the aortic dissection that occurs in the ascending aorta will be described. First, a guide wire that is not shown in the figure and the stent graft 10 that is contracted are housed within a sheath catheter that is not shown in the figure.

Figure 3:
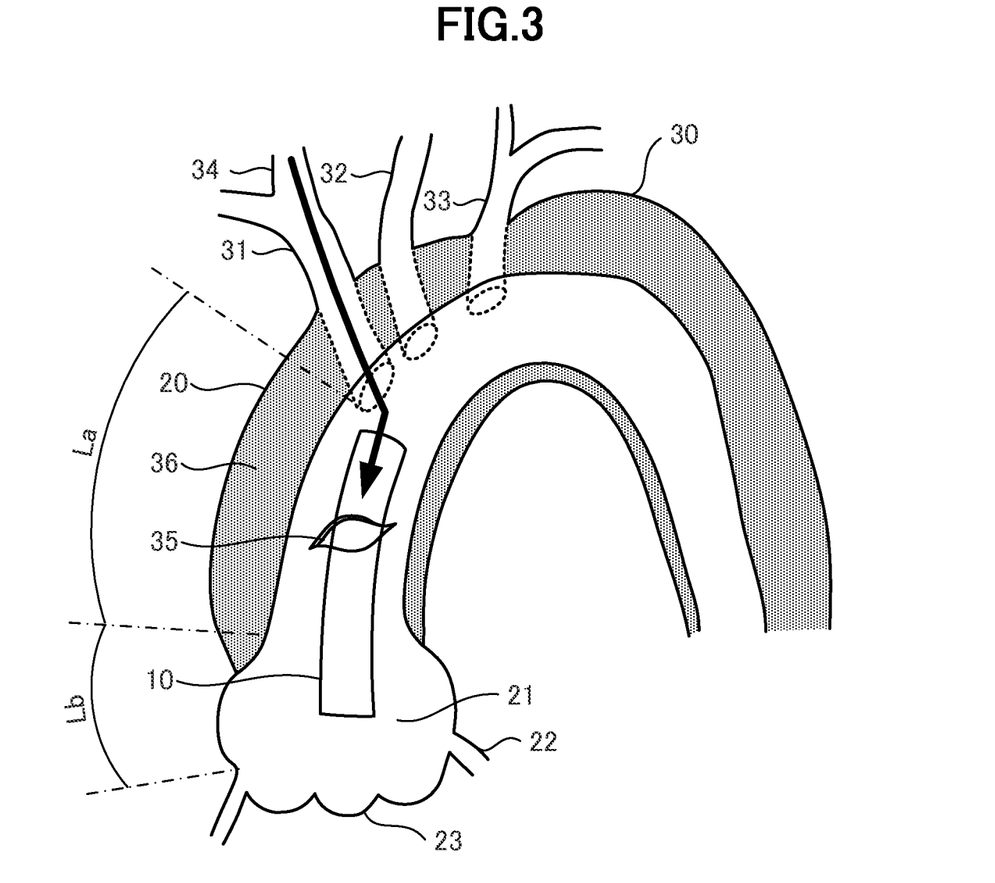
FIG. 3 is a schematic diagram showing an appearance of the stent graft in a contacted state being inserted in the ascending aorta.

First, the stent graft 10 is contracted and housed within a sheath catheter that is not shown in the figure. And, as shown in FIG. 3, the sheath catheter within which the stent graft 10 is housed is inserted from the right internal carotid artery 34. And then, the sheath catheter is, using a guide wire, carried to the ascending aorta 20 via the brachiocephalic artery 31.

The sheath catheter carried to the ascending aorta 20 is placed in an appropriate position. On this occasion, the stent graft 10 is arranged such that the boundary between the body section 11 of the stent graft 10 and the sinus of valsalva section 12 is roughly positioned at the boundary between sinus of the valsalva 21 and the ascending aorta 20.

Figure 4:
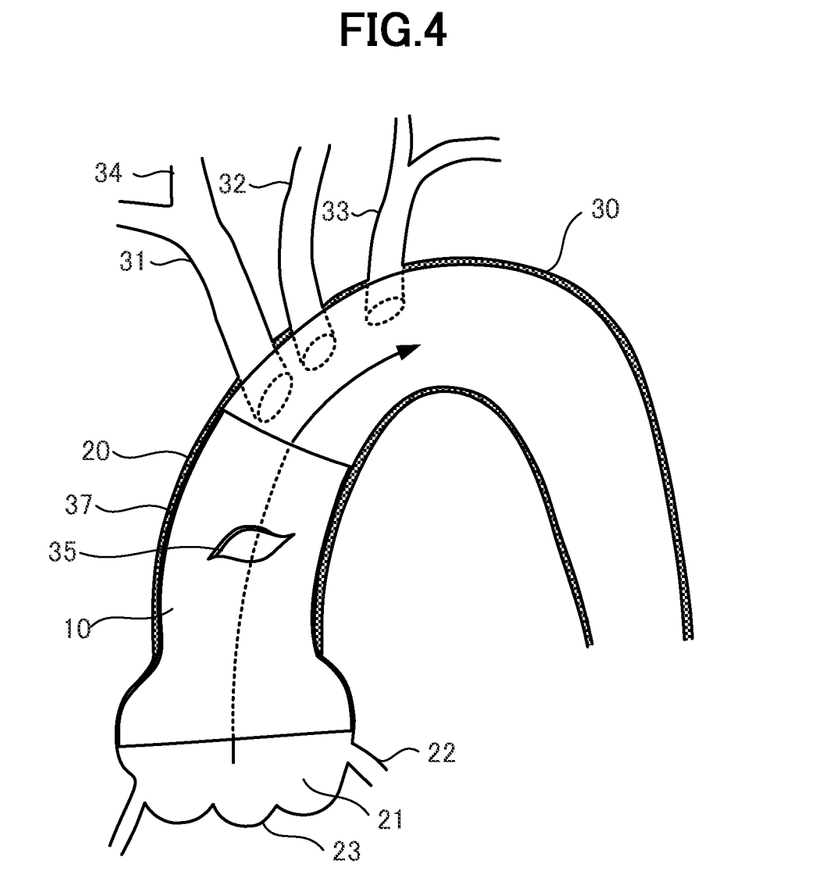
FIG. 4 is a schematic diagram of the stent graft being extended in the ascending aorta.

The stent graft 10 is thereafter released from the sheath catheter. As shown in FIG. 4, the stent graft 10 is extended. The stent graft 10 released from the sheath catheter is by oneself extended via the restoring force of the stent ST having a spring property.

When the stent graft 10 is extended, the graft material GR of the body section 11 is pushed against the inner wall of the ascending aorta 20. Thereby, the graft material GR of the body section 11 occludes the entry 35. Further, the blood flow toward the dissection cavity 36 is stopped and blood pooled in the dissection cavity 36 form the blood clot 37. Further, the body section 11 widens a narrowed cavity pocket of the ascending aorta 20 by the restoring force of the stent ST and patient's blood pressure.

Further, the graft material GR of the sinus of valsalva section 12 is pushed against the inner wall of the sinus of valsalva 21. Because the sinus of valsalva section 12 is closely attached to the wall of cylinder that forms the sinus of valsalva 21, the stent graft 10 is stably placed in the arranged position. That is, because blood flows toward the sinus of valsalva section 12 and the body section 11 as shown by the arrow in FIG. 4, the sinus of valsalva section 12 having a inner diameter larger than that of the body section 11 is caught in the sinus of valsalva 21 and stays therein. In this manner, the sinus of valsalva section 12 functions as a stopper, which thereby prevents the stent graft 10 from slipping out of position.

Further, because the length of the sinus of valsalva section 12 is formed to be shorter than the length from the boundary between the sinus of valsalva 21 and the ascending aorta 20 to the coronary artery 22, the coronary artery 22 is never occluded. Further, because the length of the body section 11 is formed to be shorter than the length from the boundary between the ascending aorta 20 and the sinus of valsalva 21 to the opening of the brachiocephalic artery 31, the brachiocephalic artery 31 is never be occluded.

As described above, the treatment of aortic dissection that occurs in ascending aorta including acute type A aortic dissection can be carried out.

It is to be noted that although a self expandable type of the stent graft 10 has been described, which self expandable type stent graft is extended by the restoring force of the stent ST having a spring property, a balloon expandable type of the stent graft 10 may be employed, which balloon expandable type stent graft is extended with a balloon being arranged inside of the stent graft 10 in the extension thereof.

Figure 5A:
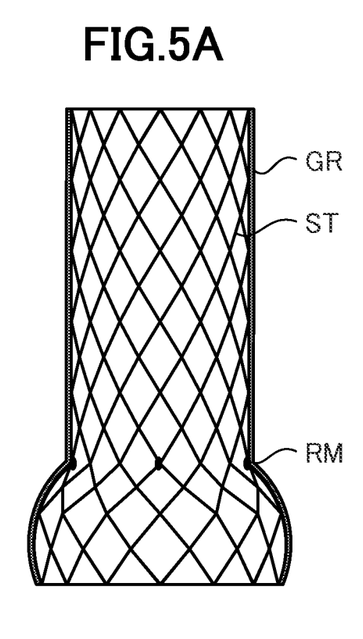
FIG. 5 is a figure showing the stent graft with roentgen markers being arranged.
Figure 5B:
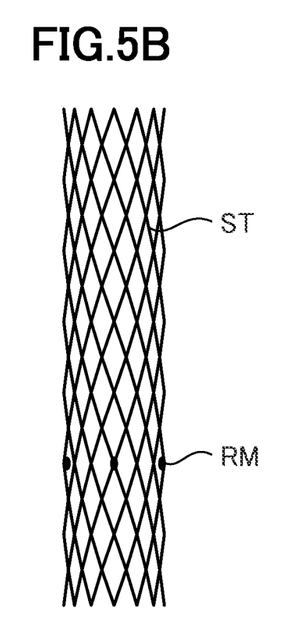

Further, as shown in FIG. 5A, the roentgen markers RMs may be arranged at the boundary between the body section 11 and the sinus of valsalva section 12. When the stent graft 10 is carried to the ascending aorta 20, it is carried and positioned in a state of being housed within a sheath catheter. But in a particular structure of the stent ST, the boundary between the body section 11 and the sinus of valsalva section 12 is hard to be recognized when the stent graft 10 is in a state of being compressed to contract. With the roentgen markers RMs being arranged at the boundary between the body section 11 and the sinus of valsalva section 12, as shown by a state subjected to X-ray photography in FIG. 5B, the boundary between the body section 11 and the sinus of valsalva section 12 is easy to be recognized. Therefore, even when the stent graft 10 is contracted in a state of being housed within a sheath catheter, the stent graft 10 can be readily arranged in an appropriate position of the ascending aorta 20. It is to be note that the composition of the roentgen marker RM will be described in detail in Embodiment 2 which is described later; and thus the explanation of the maker is left out here.

Embodiment 2

Figure 6A:
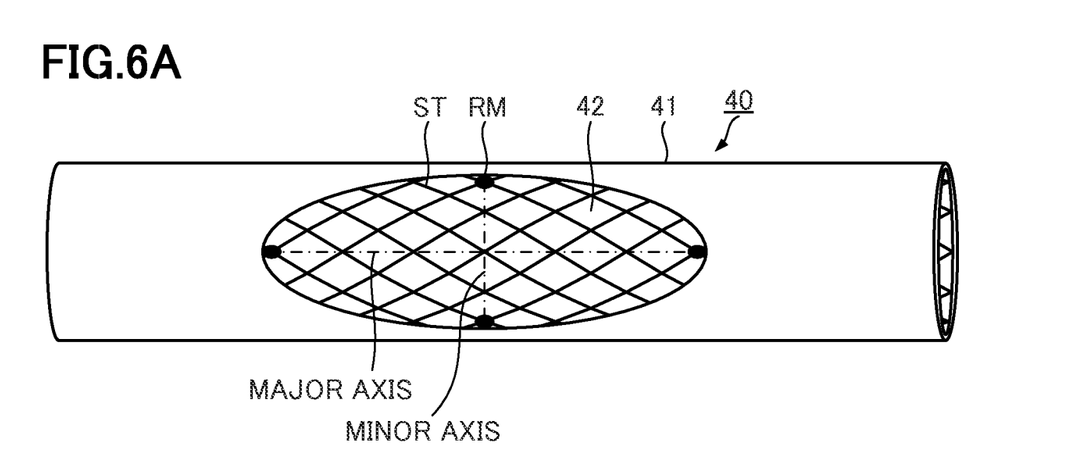
FIG. 6A is a perspective view of the stent graft in the extension thereof and FIG. 6B is a perspective view of the stent graft in the contraction thereof.
Figure 6B:
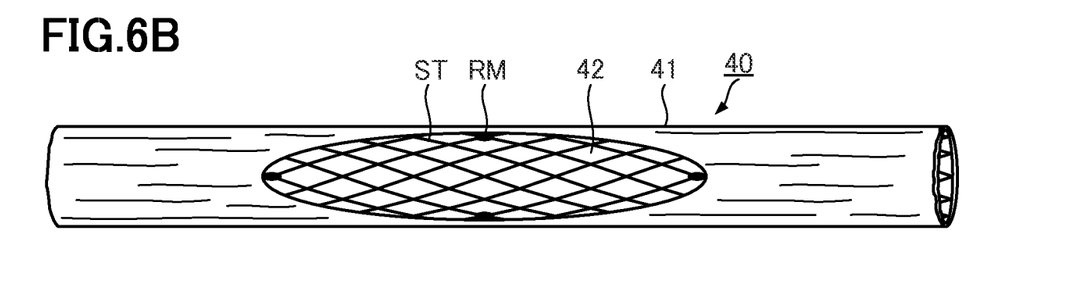

While referring to the figures, the stent graft according to Embodiment 2 will be described. The explanation will be made here by taking a stent graft used in the treatment of aortic arch aneurysm as an example. As shown in FIGS. 6A and 6B, the stent graft 40 according to the embodiment comprises the cylinder 41 having the open window 42, the stent ST, and the roentgen marker RM.

The cylinder 41 comprises a biocompatible material in the form of a film such as PTFE (Poly Tetra Fluoro Ethylene) film, silicon film, polyurethane film, or polyester film. The cylinder 41 is collapsible following stent ST's contraction and extension in a radial direction, which stent ST will be described later.

The stent ST is formed in the form of a cylinder having a spring property. The stent ST is formed so as to be contracted and extended in a radial direction with the axis of the form of the cylinder as a center. The stent ST may be formed by any style as long as it can be contracted and extended in a radial direction; and examples thereof include one formed by placing several cells apart in a direction of the axis of a cylinder, the cell being folded in a zig-zag manner to form a circular shape, one formed by linking plural cells by soldering, and one formed by cutting a metal cylinder using a laser.

Examples of materials of the stent ST include 316L stainless steel which is stainless steel for medical applications, tantalum, cobalt alloy, and nickel titanium alloy.

Further, the stent ST is connected by a known technique including suture by cyclic yarns or the like so as not to fall off from the graft material GR.

The open window 42 is formed in a part of the cylinder 41. The site of the open window 42 is in a state where the stent ST is exposed, which is a so-called bare stent. Blood becomes able to circulate from the cylinder 41 or to the cylinder 41 through this open window 42.

Figure 7:
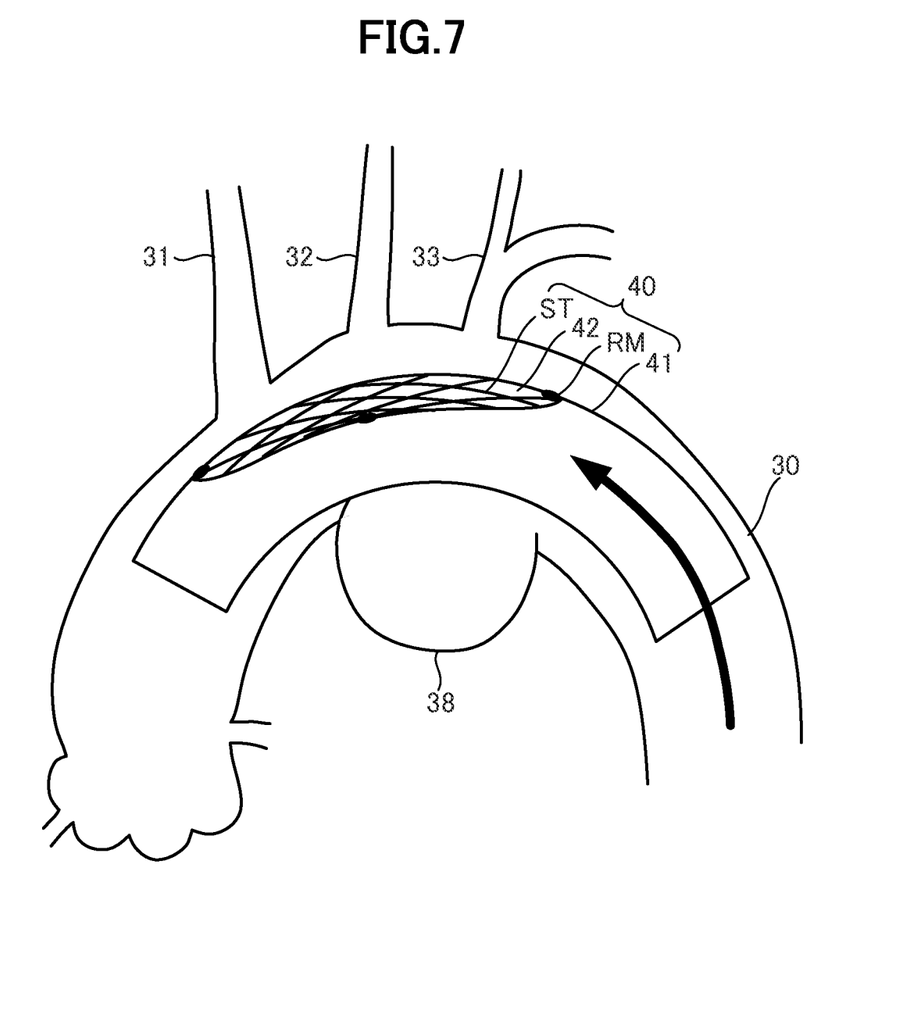
FIG. 7 is a schematic diagram showing an appearance of the stent graft being inserted in the aortic arch.

As shown in FIG. 7, the aortic arch aneurysm 38 generally occurs in the lesser curvature side of the aortic arch 30. And, there are, in the greater curvature side of the aortic arch 30, the brachiocephalic artery 31, the left common carotid artery 32, and the left subclavian artery 33 branching from the aortic arch 30. Because the open window 42 must try not to interfere with blood flow from the aortic arch 30 to the brachiocephalic artery 31, the left common carotid artery 32, and the left subclavian artery 33, with three of the openings of the brachiocephalic artery 31, the left common carotid artery 32, and the left subclavian artery 33 being regarded as one compartment, the open window 42 may be formed so as to have an approximate size to enclose this compartment.

The material, shape, and size of the roentgen marker RM are not restricted as long as it is one that can be recognized at the time of X-ray photography, that is, one that does not allow X rays to pass through, and one that does not impair the function of the stent ST. Further, examples of the material of the roentgen marker RM include metals such as stainless steel, titanium, and the same materials as those of the stent ST described above. The roentgen marker RM may be arranged by any method as long as it does not come off the stent ST; and examples of the method include soldering to the stent ST. Further, a wire that is integrally formed with the roentgen marker RM may be provided to form the stent ST.

For instance, as shown in FIG. 6A, in the case in which the open window 42 is elongated circular such as oval, the roentgen markers RMs may be arranged in each of both edges of the major axis and both edges of the minor axis. Further, the roentgen markers RMs are preferably arranged at the inside of the open window 42.

By the above composition, as shown in FIG. 6B, the stent graft 40 is altogether contracted when compressed in a radial direction with the axis of the cylinder as a center. Thereby, the stent graft 40 can be housed within a sheath catheter and at the same time can become stick to the inner wall of the aorta when extended.

Subsequently, endovascular aortic repair using the stent graft 40 in the treatment of aortic arch aneurysm will be described. First, a guide wire that is not shown in the figure and the stent graft 40 that is contracted are housed within a sheath catheter that is not shown in the figure.

The groin at the top of one of patient's legs is incised and the sheath catheter is inserted therefrom into an artery. And, as shown in FIG. 7, it is moved to the site where the aortic arch aneurysm 38 is formed using the guide wire.

Figure 8:
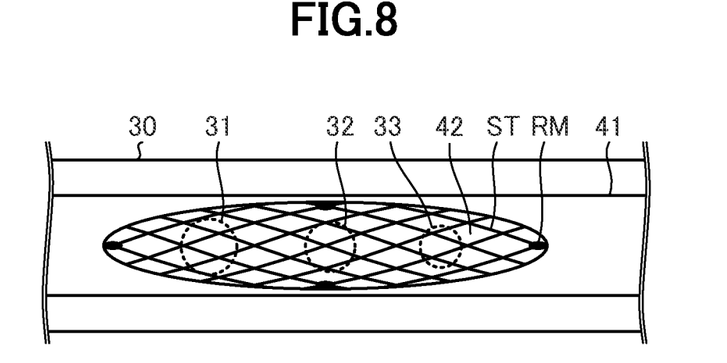
FIG. 8 is a schematic diagram showing an appearance of the stent graft being inserted in the aortic arch, which is viewed from the greater curvature side of the aortic arch.

And, when the stent graft 40 is extended, the stent graft 40 is arranged in the position where the cylinder 41 occludes the aortic arch aneurysm 38 but does not occlude the openings of the brachiocephalic artery 31, the left common carotid artery 32, and the left subclavian artery 33. For instance, as shown in FIG. 8, the stent graft is adjusted such that the open window 42 encloses all of the openings the brachiocephalic artery 31, the left common carotid artery 32, and the left subclavian artery 33.

Figure 9:
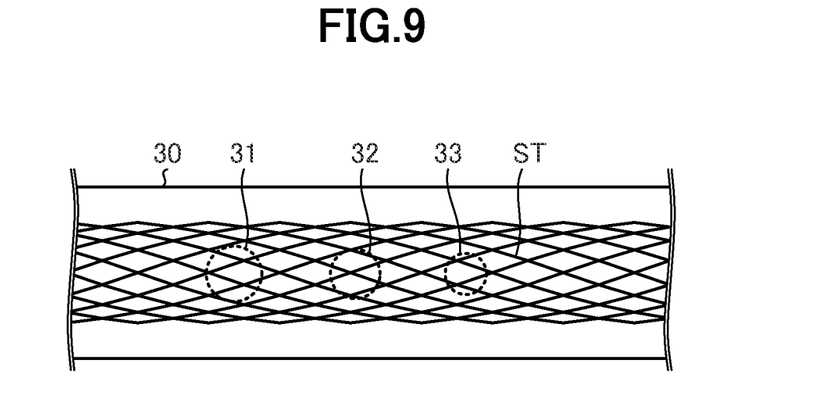
FIG. 9 is a schematic diagram of x-ray photography when the stent graft without roentgen markers is inserted in the aortic arch.

Here, FIG. 9 schematically shows a state where a stent graft that does not have the roentgen marker RM is inserted into the aortic arch 30 and subjected to X-ray photography; and a cylinder comprising a graft material is not in a picture of X-ray photography and only the stent ST is. That is, even if an open window is formed in a cylinder, the position of the open window cannot be recognized. It is therefore difficult to place the stent graft such that the open window encloses the openings of the brachiocephalic artery 31, the left common carotid artery 32, and the left subclavian artery 33.

Figure 10:
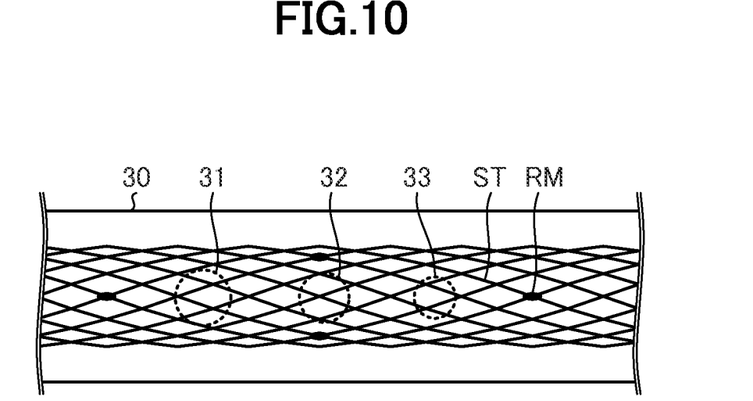
FIG. 10 is a schematic diagram of x-ray photography when the stent graft with roentgen markers is inserted in the aortic arch.

In the meantime, FIG. 10 schematically shows a state where the stent graft 40 according to the present embodiment is inserted into the aortic arch 30 and subjected to X-ray photography; and because the stent graft 40 comprises the roentgen markers RMs along the open window 42, the roentgen markers RMs are captured in a picture upon the X-ray photography. It can be recognized that a circle formed by connecting four roentgen markers RMs is the peripheral of the open window 42. Thereby, a positional relationship between the open window 42 and the openings of the brachiocephalic artery 31, the left common carotid artery 32, and the left subclavian artery 33 can be recognized; and a position in which the stent graft 40 is extended can be readily adjusted in the aortic arch 30.

Figure 11:
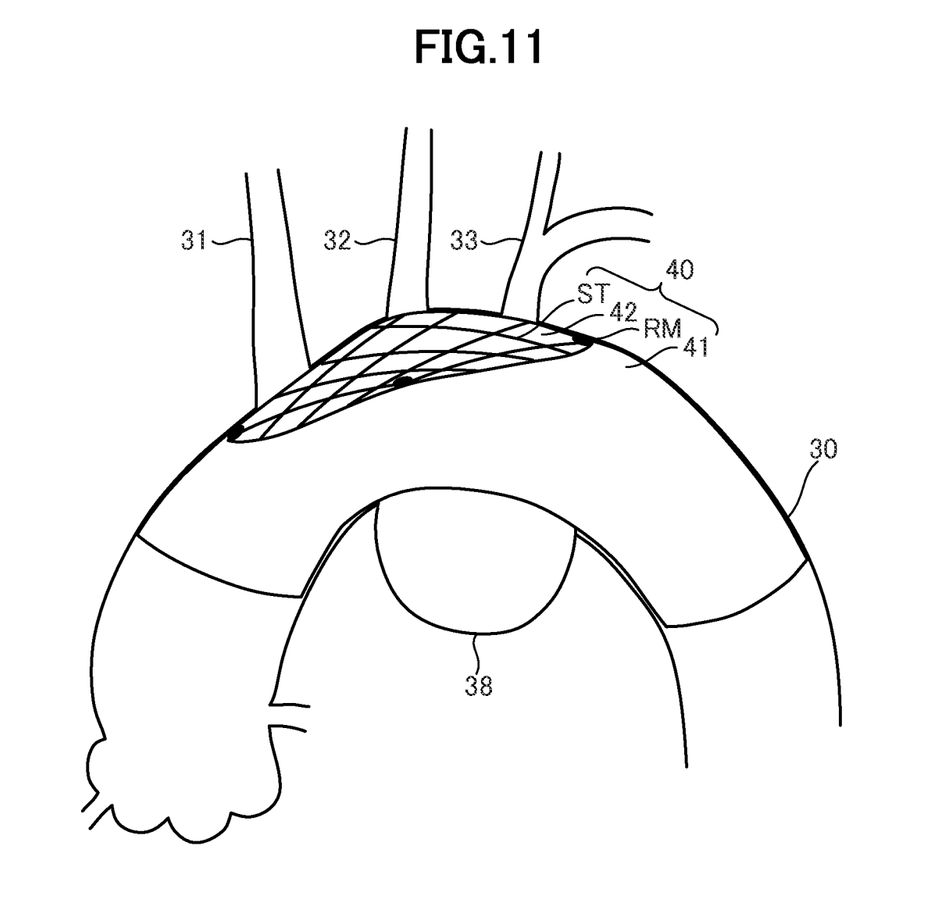
FIG. 11 is a schematic diagram showing an appearance of the stent graft being extended in the aortic arch.

After the position of the stent graft 40 is determined, the stent graft 40 is released from the catheter. As shown in FIG. 11, the stent graft 40 is extended. Because the stent ST has a spring property, the stent graft is extended by its own elastic force and pushes the cylinder 41 against the arterial wall of the aortic arch 30. And, the cylinder 41 occludes the aortic arch aneurysm 38.

Figure 12:
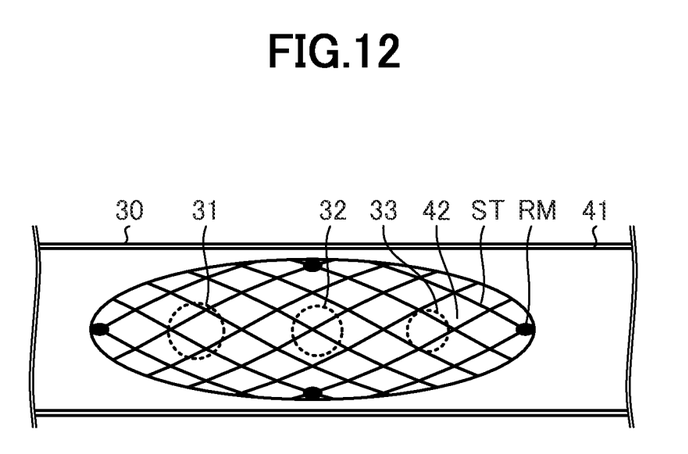
FIG. 12 is a schematic diagram showing an appearance of the stent graft being inserted in the aortic arch, which is viewed from the greater curvature side of the aortic arch.

Further, as shown in FIG. 12, the stent graft is placed such that the open window 42 encloses all of the openings of the brachiocephalic artery 31, the left common carotid artery 32, and the left subclavian artery 33. Blood flows from the aortic arch 30 to the brachiocephalic artery 31, the left common carotid artery 32, and the left subclavian artery 33 through the open window 42.

Further, because the site of the open window 42 is a bare stent, no gaps are generated between the open window 42 and the aortic arch 30, which thus prevents blood leak.

In this way, endovascular aortic repair can be carried out. In the above endovascular aortic repair, the aortic arch aneurysm 38 is not surgically removed and remains; but the aneurysm comes to be covered by the stent graft 40. Blood flowing inside the aortic arch aneurysm 38 disappears and the aneurysm becomes gradually smaller.

It is to be noted that although the example in which four roentgen markers RMs are arranged in four edges of the open window 42 has been described above, the number of the roentgen markers RMs is not restricted and more roentgen markers RMs may be arranged around the periphery of the open window 42.

Further, the explanation has been made by taking the mode of the stent ST being arranged on the inner circumference of the cylinder 41 as an example; but a mode of the stent ST being arranged on the outer circumference of the cylinder 41 may be employed.

It is to be noted that although a self expandable type of the stent graft 40 has been described, which self expandable type stent graft is extended by the restoring force of the stent ST having a spring property, a balloon expandable type of the stent graft 40 may be employed, which balloon expandable type stent graft is extended with a balloon being arranged inside of the stent graft 40 in the extension thereof.

It is to be noted that various embodiments and variations of the present disclosure can be made without departing from the scope of the present disclosure. Further, the embodiments described above are for the purpose of illustrating the present disclosure and by no means limit the scope of the present disclosure.

The present application is based on Japanese Patent Application No. 2012-040771 which is filed on Feb. 27, 2012. The specification, claims, and drawings of Japanese Patent Application No. 2012-040771 are herein incorporated by reference in their entirety.

INDUSTRIAL APPLICABILITY

A stent graft having a sinus of valsalva section and body section can be used in the treatment of aortic dissection that occurs in the ascending aorta or the like, because the body section occludes a tear generated in the aorta and the sinus of valsalva section concurrently functions as a stopper.

Further, when a stent graft having an open window and roentgen markers around the periphery of stent graft's open window is used, the position of open window can be readily recognized even in the state where the stent graft is contracted and housed within a sheath catheter. Because of this, it can be used in the treatment of aortic aneurysm in a region where the openings of arteries branching from the periphery of the aneurysm such as aortic arch aneurysms are present.

REFERENCE SIGNS LIST

10 Stent graft
11 Body section
12 Sinus of valsalva section
20 Ascending aorta
21 Sinus of valsalva
22 Coronary artery
23 Aortic valve
30 Aortic arch
31 Brachiocephalic artery
32 Left common carotid artery
33 Left subclavian artery
34 Right internal carotid artery
35 Entry
36 Dissection cavity
37 Blood clot
38 Aortic arch aneurysm
40 Stent graft
41 Cylinder
42 Open window
ST Stent
GR Graft material
RM Roentgen marker

The invention claimed is:

1. A stent graft comprising a cylinder comprising a graft material in the form of a film, and a stent that supports the cylinder, characterized in that:
the stent graft is configured to be inserted within a region from an ascending aorta to a sinus of valsalva; and
the stent graft comprises a first side end portion and a second side end portion, wherein the first side end portion is a cylindrical body section configured to be arranged in the ascending aorta, and the second side end portion is a sinus of valsalva section configured to be arranged in the sinus of valsalva, wherein the sinus valsalva section has an inner diameter larger than an inner diameter of the cylindrical body section, wherein the inner diameter of the sinus valsalva section expands towards a tip without the inner diameter decreasing in size, and only the sinus valsalva section has a substantially bowl shaped cross-section in a configuration when the entire stent graft is extended.

2. The stent graft according to claim 1, wherein the sinus of valsalva section has a length shorter than the length from the boundary between the sinus of valsalva and the ascending aorta to the opening of coronary artery.

3. The stent graft according to claim 1, wherein the body section has a length shorter than the length from the boundary between the sinus of valsalva and the ascending aorta to the opening of brachiocephalic artery.

4. The stent graft according to claim 1, wherein roentgen markers are arranged at the boundary between the body section and the sinus of valsalva section.

5. A stent graft comprising a cylinder comprising a graft material in the form of a film, and a stent that supports the cylinder, characterized in that:
the stent graft is configured to be inserted within a region from an ascending aorta to a sinus of valsalva; and
the stent graft comprises a first side end portion and a second side end portion, wherein the first side end portion is a cylindrical body section configured to be arranged in the ascending aorta, and the second side end portion is a sinus of valsalva section configured to be arranged in the sinus of valsalva, wherein the sinus valsalva section has an inner diameter larger than an inner diameter of the cylindrical body section, wherein the sinus of valsalva section has a length shorter than the length from the boundary between the sinus of valsalva and the ascending aorta to the opening of coronary artery, and only the sinus valsalva section has a substantially bowl shaped cross-section in a configuration when the entire stent graft is extended.

6. A stent graft comprising a cylinder comprising a graft material in the form of a film, and a stent that supports the cylinder, characterized in that:
the stent graft is configured to be inserted within a region from an ascending aorta to a sinus of valsalva; and
the stent graft comprises a first side end portion and a second side end portion, wherein the first side end portion is a cylindrical body section configured to be arranged in the ascending aorta, and the second side end portion is a sinus of valsalva section configured to be arranged in the sinus of valsalva, wherein the sinus valsalva section has an inner diameter larger than an inner diameter of the cylindrical body section, wherein the body section has a length shorter than the length from the boundary between the sinus of valsalva and the ascending aorta to the opening of brachiocephalic artery, and only the sinus valsalva section has a substantially bowl shaped cross-section in a configuration when the entire stent graft is extended.

* * * * *

UNITED STATES PATENT AND TRADEMARK OFFICE
CERTIFICATE OF CORRECTION

PATENT NO. : 10,828,144 B2
APPLICATION NO. : 14/381392
DATED : November 10, 2020
INVENTOR(S) : Sueda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 805 days.

Signed and Sealed this
Sixth Day of December, 2022

Katherine Kelly Vidal
*Director of the United States Patent and Trademark Office*